US009764034B2

(12) United States Patent
Iyoha et al.

(10) Patent No.: US 9,764,034 B2
(45) Date of Patent: *Sep. 19, 2017

(54) ORAL COMPOSITION COMPRISING A COOLING AGENT

(71) Applicant: Reckitt Benckiser Healthcare (UK) Limited, Slough, Berkshire (GB)

(72) Inventors: Kingsley Iyoha, Manchester (GB); Neil Campbell Muir, Manchester (GB); Robert Rhoades, Kimberley (GB); Alden Rodwell, Hull (GB); David Michael Thurgood, Long Eaton (GB)

(73) Assignee: RECKITT BENCKISER HEALTHCARE (UK) LIMITED, Slough (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/131,314

(22) Filed: Apr. 18, 2016

(65) Prior Publication Data

US 2016/0228552 A1  Aug. 11, 2016

Related U.S. Application Data

(63) Continuation of application No. 12/738,178, filed as application No. PCT/GB2008/003543 on Oct. 17, 2008, now Pat. No. 9,314,428.

(30) Foreign Application Priority Data

Oct. 19, 2007 (GB) .................................. 0720425.8

(51) Int. Cl.

| | | |
|---|---|---|
| A61K 47/26 | (2006.01) |
| A61K 31/05 | (2006.01) |
| A61K 31/55 | (2006.01) |
| A61K 31/485 | (2006.01) |
| A61K 31/09 | (2006.01) |
| A23G 4/06 | (2006.01) |
| A61K 8/02 | (2006.01) |
| A61K 8/34 | (2006.01) |
| A61K 9/00 | (2006.01) |
| A61K 31/00 | (2006.01) |
| A61Q 11/00 | (2006.01) |
| A61K 31/045 | (2006.01) |
| A61K 31/055 | (2006.01) |
| A61K 31/137 | (2006.01) |
| A61K 31/167 | (2006.01) |
| A61K 31/192 | (2006.01) |
| A61K 31/245 | (2006.01) |
| A61K 31/4425 | (2006.01) |
| A61K 31/4706 | (2006.01) |
| A61K 9/68 | (2006.01) |

(52) U.S. Cl.
CPC ................ *A61K 47/26* (2013.01); *A23G 4/06* (2013.01); *A61K 8/0216* (2013.01); *A61K 8/345* (2013.01); *A61K 9/0053* (2013.01); *A61K 9/0056* (2013.01); *A61K 31/00* (2013.01); *A61K 31/045* (2013.01); *A61K 31/05* (2013.01); *A61K 31/055* (2013.01); *A61K 31/09* (2013.01); *A61K 31/137* (2013.01); *A61K 31/167* (2013.01); *A61K 31/192* (2013.01); *A61K 31/245* (2013.01); *A61K 31/4425* (2013.01); *A61K 31/4706* (2013.01); *A61K 31/485* (2013.01); *A61Q 11/00* (2013.01); *A61K 9/006* (2013.01); *A61K 9/0058* (2013.01); *A61K 2800/244* (2013.01)

(58) Field of Classification Search
IPC .................. A61K 47/26,31/05, 31/485, 31/167, A61K 31/09
See application file for complete search history.

(56) References Cited

U.S. PATENT DOCUMENTS

| | | |
|---|---|---|
| 2005/0260266 A1 | 11/2005 | Gebreselassie et al. |
| 2007/0081949 A1 | 4/2007 | Dam et al. |
| 2007/0098648 A1* | 5/2007 | Haley .................... A61K 9/006 424/48 |
| 2007/0196496 A1 | 8/2007 | Farber et al. |
| 2009/0081294 A1 | 3/2009 | Gin et al. |

FOREIGN PATENT DOCUMENTS

| | | |
|---|---|---|
| EP | 0922464 A1 | 6/1999 |
| EP | 1008353 A1 | 6/2000 |
| EP | 1329217 A1 | 7/2003 |
| WO | 0061117 A1 | 10/2000 |
| WO | 2004089343 A1 | 10/2004 |
| WO | 2005067906 A2 | 7/2005 |
| WO | 2006063189 A2 | 6/2006 |
| WO | 2007055427 A1 | 5/2007 |
| WO | 2007066178 A2 | 6/2007 |
| WO | 2007110871 A2 | 10/2007 |

OTHER PUBLICATIONS

International Search Report dated Feb. 18, 2000 for priority application PCT/GB2008/003543.
International Preliminary Report on Patentability and Written Opinion by Dorothee Mulhausen, dated Apr. 20, 2010.

* cited by examiner

*Primary Examiner* — Shirley V Gembeh
(74) *Attorney, Agent, or Firm* — Troutman Sanders LLP; Ryan Schneider; Chris Davis

(57) ABSTRACT

The present invention relates to a formulation comprising an endothermic cooling agent selected from the group consisting of xylitol, sorbitol, mannitol and erythritol having a heat of enthalpy between −10 cal/g and −100 cal/g, and one or more active agents wherein the endothermic agent is present in the formulation at an amount less than 10% w/w.

10 Claims, No Drawings

ORAL COMPOSITION COMPRISING A COOLING AGENT

CROSS-REFERENCE TO RELATED APPLICATIONS

This application is a continuation of U.S. Ser. No. 12/738,178 filed 17 May 2010, now U.S. Pat. No. 9,314,428, which is a US National Stage of International Application No. PCT/GB2008/003543, filed 17 Oct. 2008, which claims the benefit of GB 0720425.8, filed 19 Oct. 2007, all of which are herein fully incorporated by reference.

FIELD OF THE INVENTION

The present invention relates to an oral composition which contains a cooling agent. In particular, the present invention relates to medicament containing a cooling agent. More particularly, the present invention relates to a medicament for treating sore throats which contains xylitol.

BACKGROUND OF THE INVENTION

Cooling agents have been used in a number of different formulations, such as hard confectionary products or oral gums, to provide a pleasant taste and a cooling sensation. For example, compounds such as menthol or peppermint oil have been used in either as part of the formulation or as part of a coating in order to provide the user with a cooling sensation.

Cooling agents have also been used in pharmaceutical formulations to enhance the physiological and/or perceived benefits, such as speed or duration of relief. Such agents are commonly used in non-prescription cough medicines.

Sore throats are generally treated using pharmaceutical lozenges containing a therapeutically effective amount of an active compound. Suitably, the lozenge is sucked by a patient in need of such treatment and the active is released in the oral cavity and delivered to the surface of the sore throat (i.e., mucous membrane).

Some of the actives which are used to relieve the symptoms associated with a sore throat can cause an unpleasant burning sensation at the back of the mouth when retained in the mouth, e.g., a non-steroidal anti-inflammatory drug (NSAID). This is unacceptable to the patient being treated. Consequently, pharmaceutical lozenges containing actives such as an NSAID have been devised where the lozenge formed therefrom relieves the symptoms of a sore throat but the patient does not experience an unacceptable burning sensation.

Cooling agents have also been used with sweeteners in liquid cough-treatment compositions. The limited portability of liquids limits the use of coolants in liquid compositions, and some high-intensity sweeteners, such as aspartame, are subject to degradation when heated.

In addition, the cooling agent itself can result in a burning effect if used at too high a level in the composition.

The cooling effect or sensation of cooling in the mouth is usually achieved using a polyol. The effect is caused by the negative heat of dissolution of such polyols in water, and is also linked to their rate of dissolution. Crystalline xylitol is in this respect particularly effective since it confers the most intense cooling sensation. Sorbitol and erythritol have slightly lower cooling effects than xylitol.

Xylitol, also called wood sugar or birch sugar, is a five-carbon sugar alcohol that can be used as a sugar substitute. It is derived from various types of cellulose products, such as wood, straw, cane pulp, seed hulls and shells. Xylitol is an odourless, sweet tasting granular solid (comprising crystalline, equi-dimensional particles). Xylitol has a sweetness level equivalent to sugar. The combination of a relatively large negative heat of solution and high solubility means that xylitol provides cooling sensation in the mouth that is said to be refreshing.

Sorbitol is a popular bulk sweetener found in numerous food products. In addition to providing sweetness, it is an excellent humectant and texturizing agent. Mannitol is a monosaccharide polyol. Both sorbitol and mannitol are generally stable and chemically unreactive.

The main disadvantage of xylitol is that it is an expensive ingredient. In addition, it is generally understood that a cooling effect will only be obtained when using crystalline xylitol. Accordingly, xylitol is often replaced with a less expensive sugarless polyol, such as sorbitol.

BRIEF SUMMARY OF THE INVENTION

The use of sorbitol is well-known and described. There are numerous Patent publications disclosing such a use, for example GB 2 115 672, U.S. Pat. No. 4,317,838 and U.S. Pat. No. 4,753,790.

It would be desirable to be able to use xylitol in a lower amount. However, it is thought that the presence of a small quantity of xylitol in a formulation would not produce a significant sensation of coolness.

In one embodiment of the invention is provided a formulation comprising an endothermic cooling agent having a heat of enthalpy between −10 cal/g and −100 cal/g, and one or more active agents wherein the endothermic agent is present in the formulation at an amount less than 10% w/w.

In some embodiments, the endothermic cooling agent has a heat of enthalpy in the range −10 cal/g to −50 cal/g. In other embodiments, the endothermic cooling agent has a heat of enthalpy in the range −20 cal/g to −35 cal/g.

In some embodiments, the endothermic cooling agent is present in the formulation at an amount in the range of 1-5%. In other embodiments, the endothermic cooling agent is present in the formulation at an amount in the range of 1-3%.

In some embodiments, the endothermic cooling agent is selected from the group consisting of xylitol, sorbitol, mannitol and erythritol.

In some embodiments, the one or more active agents is selected from the group consisting of hexylresorcinol, flurbiprofen, lidocaine, benzocaine, cetylpyridinium chloride, dequalinium chloride, menthol, ambroxol hydrochloride, dextromethorphan hydrobromide and guaifenesin.

In some embodiments, the formulation is selected from the group consisting of a lozenge, gel, spray, capsule, pastille, gum and tablet.

In some embodiments, the formulation contains one or more additional excipients selected from the group consisting of acidity regulators, opacifiers, colouring agents, stabilising agents, buffering agents, sweeteners, flavourings and preservatives.

In another aspect of the invention, the invention comprises the use of an endothermic cooling agent having a heat of enthalpy between −10 cal/g and −100 cal/g in a medicament wherein the endothermic agent is present in the medicament at an amount less than 10% w/w.

In yet another aspect of the invention, the invention comprises the use of an endothermic cooling agent having a heat of enthalpy between −10 cal/g and −100 cal/g for the preparation of a medicament for the treatment of a sore throat.

DETAILED DESCRIPTION OF THE INVENTION

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or examples. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example.

According to a first aspect of the present invention there is provided a formulation comprising an endothermic cooling agent having a heat of enthalpy between −10 cal/g and −100 cal/g, and one or more active agents wherein the endothermic agent is present in the formulation at an amount less than 10% w/w.

The endothermic cooling agent can have a heat of enthalpy in the range −10 cal/g to −50 cal/g. A more preferred endothermic cooling agent can have a heat of enthalpy in the range −20 cal/g to −35cal/g.

The endothermic cooling agent can be present in the medicament at an amount in the range of from 1-5%. A preferred range is from 1-3%.

The endothermic cooling agent can be a polyol, preferably selected from the group consisting of xylitol, sorbitol, mannitol and erythritol.

The active agent is preferably selected from the group comprising, but not limited to, 2,4-dichlorobenzyl alcohol (DCBA), amyl metacresol (AMC), hexylresorcinol, flurbiprofen, lidocaine, benzocaine, cetylpyridinium chloride, dequalinium chloride, menthol, ambroxol hydrochloride, dextromethorphan hydrobromide and guaifenesin.

The formulation can be in any suitable form including lozenge, gel, spray, capsule, pastille, gum or tablet.

The agent can form part of a coating when the formulation is in a form which is suitable for coating.

Preferably the formulation does not contain a high intensity sweetener.

The formulation may contain additional excipients as required. Typical excipients include, but are not limited to, acidity regulators, opacifiers, colouring agents, stabilising agents, buffering agents, sweeteners, flavourings and preservatives.

According to a second aspect of the present invention there is provided the use of an endothermic cooling agent having a heat of enthalpy between −10 cal/g and −100 cal/g in a medicament wherein the endothermic agent is present in the medicament at an amount less than 10% w/w.

The endothermic cooling agent can have a heat of enthalpy in the range −10 cal/g to −50 cal/g. A more preferred endothermic cooling agent can have a heat of enthalpy in the range −20 cal/g to −35 cal/g.

The endothermic cooling agent can be present in the medicament at an amount in the range of from 1-5%. A preferred range is from 1-3%.

The endothermic cooling agent can be a polyol, preferably selected from the group consisting of xylitol, sorbitol, mannitol and erythritol The active agent is preferably selected from the group comprising 2,4-dichlorobenzyl alcohol (DCBA), amyl metacresol (AMC), hexylresorcinol, flurbiprofen, lidocaine, benzocaine, cetylpyridinium chloride, dequalinium chloride, menthol, ambroxol hydrochloride, dextromethorphan hydrobromide and guaifenesin.

The medicament can be in any suitable form including lozenge, gel, spray, capsule, pastille or gum.

The agent may form part of a coating when the medicament is in a form which is suitable for coating.

Preferably the medicament does not contain a high intensity sweetener.

The medicament may contain additional excipients as required. Typical excipients include, but are not limited to, acidity regulators, opacifiers, colouring agents, stabilising agents, buffering agents, sweeteners, flavourings and preservatives.

According to a third aspect of the present invention there is provided a use of an endothermic cooling agent for the preparation of the medicament of the second aspect of the present invention for the treatment of a sore throat.

The preferred form of the present invention is a solid form, such as a lozenge, which can be sucked or chewed thus releasing the endothermic cooling agent in the mouth of a patient. The cooling agent can then pass over the surface of the throat and provide relief to a patient.

In the context of the present invention the term 'endothermic cooling agent' as use herein refers to a compound, such as xylitol, which actually cools the body locally as a result of having a significant negative heat of dissolution. In contrast compounds such as menthol are generally referred to as a 'physiological cooling agent' on the basis that they cause the body to perceive a low temperature even though this is usually erroneous.

For the avoidance of doubt the formulations as defined in the first aspect of the invention includes confectionery products, food supplements and foodstuffs, nutraceuticals, medicinal and non-medicinal products wherein non-medicinal products includes products which would not be considered as confectionery products, e.g. non-prescription lozenges for the treatment of conditions such as sore throats.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example Formulation

| Standard Name | mg | % |
| --- | --- | --- |
| Sucrose/Glucose Syrup | 2481.06 | 95.42% |
| Xylitol | 40 | 1.54% |
| Flavouring | 18 | 0.70% |
| Levomethol Ph Eur Natural | 8 | 0.31% |
| 2,4-Dichlorobenzyl Alcohol | 1.2 | 0.05% |
| Amylmetacresol BP | 0.615 | 0.02% |
| Eucalyptus Oil Ph Eur | 0.5 | 0.02% |
| Total (incl. theoretical 2% moisture) | 2600 | 100% |

The lozenges are prepared using a process based on mixing constant streams of ingredients, which is conventional for the high-speed manufacture of high-boiled lozenge products. The liquid sucrose and the liquid glucose are mixed to form a syrup, which is fed into a holding vessel. The syrup is then pumped from the holding vessel into the cooker system, where the water content is reduced which results in the formation of the lozenge base. The lozenge base is drawn from the cooker in a continuous stream and fed into the mixing chamber; lozenge essence (containing active ingredients and flavour) is added with crystalline xylitol at a rate proportional to the flow of the lozenge base. This forms the lozenge mass.

The lozenge mass then flows continuously from the mixing chamber onto a tempering belt where it is cooled prior to lozenge formation and further cooling.

Alternative dosage forms, e.g. a chewable solid dosage form, can be produced using methods well-known and described to the man skilled in the art.

To demonstrate a localised physical cooling of lozenges containing xylitol, various samples of lozenges were prepared in the laboratory.

The following lozenges were made:
1. Plain Sugar-glucose lozenges
2. Sugar-glucose lozenges containing levomenthol (8 mg per 2.6 g lozenge)
3. Sugar-glucose lozenges containing Xylitol (40 mg per 2.6 g lozenge 1.5% w/w)
4. Sugar-glucose lozenges containing Xylitol (40 mg per 2.6 g lozenge 4.6% w/w)

The plain sugar-glucose lozenges were included in the experiment as a reference point for this cooling. As xylitol provides cooling via a different mechanism to menthol, samples containing menthol were also included in this experiment to highlight this difference.

The samples of lozenges identified above (i.e. 1-4) were tasted by a number of individuals.

The participants were asked to indicate whether they got a sense of cooling on the surface of the lozenge when in contact with any part of the mouth. The participants were also asked to rank from 1 to 4 (most cool-4 least cool) the surface cooling of the lozenges.

The table below indicates how the participants scored the samples in terms service coolness. A score of 1 is considered the most cool, whereas a score of 4 is the least cool.

| Participant | Lozenge 1 | Lozenge 2 | Lozenge 3 | Lozenge 4 |
|---|---|---|---|---|
| 1 | 4 | 3 | 2 | 1 |
| 2 | 4 | 3 | 2 | 1 |
| 3 | 4 | 3 | 1 | 2 |
| 4 | 4 | 3 | 2 | 1 |
| 5 | 4 | 3 | 2 | 1 |

KEY
Lozenge 1 - Plain Sugar-glucose lozenges
Lozenge 2 - Sugar-glucose lozenges containing levomenthol
Lozenge 3 - Sugar-glucose lozenges containing Xylitol (40 mg per 2.6 g lozenge 1.5% w/w)
Lozenge 4 - Sugar-glucose lozenges containing Xylitol (120 mg per 2.6 g lozenge 4.6% w/w)

Each participant perceived surface cooling to be exhibited most in the lozenges containing xylitol. The majority of participants were able to identify the lozenge with the higher quantity of xylitol as being the most cooling.

Accordingly the presence of xylitol in a lozenge at low concentrations (1.5% w/w-4.6% w/w) results in the lozenge exhibiting unexpectedly strong cooling properties.

Generally, any polyol may be used in the present invention as they have a sweet taste and can be used to provide a cooling effect in the mouth. Commonly-used polyols include xylitol, mannitol, sorbitol and erythritol. However, the man skilled in the art will recognize that a variety of polyols and combinations of polyols may be used.

In an alternative embodiment the actives, components DCBA and AMC, can be replaced by flurbiprofen, hexylresorcinol, lidocaine, benzocaine, cetylpyridinium chloride, dequalinium chloride, menthol, ambroxol hydrochloride, dextromethorphan hydrobromide or guaifenesin.

While several possible embodiments are disclosed above, embodiments of the present invention are not so limited. These exemplary embodiments are not intended to be exhaustive or to unnecessarily limit the scope of the invention, but instead were chosen and described in order to explain the principles of the present invention so that others skilled in the art may practice the invention. Indeed, various modifications of the invention in addition to those described herein will become apparent to those skilled in the art from the foregoing description. Such modifications are intended to fall within the scope of the appended claims. For instance, while several possible configurations of materials for the formulation have been disclosed, other suitable materials and combinations of materials could be selected without departing from the spirit of embodiments of the invention. Such changes are intended to be embraced within the scope of the invention.

The embodiments of the present invention are also not limited to the particular formulations, process steps, and materials disclosed herein as such formulations, process steps, and materials may vary somewhat. Further, the terminology employed herein is used for the purpose of describing exemplary embodiments only and the terminology is not intended to be limiting since the scope of the various embodiments of the present invention will be limited only by the appended claims and equivalents thereof.

All patents, applications, publications, test methods, literature, and other materials cited herein are hereby incorporated by reference in their entirety as if physically present in this specification.

What is claimed is:

1. A formulation comprising:
    an endothermic cooling agent having a heat of enthalpy between −10 cal/g and −100 cal/g, and one or more active agents,
    wherein the endothermic cooling agent is present in the formulation at an amount in the range of 1-5% w/w.

2. The formulation as claimed in claim 1 wherein the endothermic cooling agent has a heat of enthalpy in the range −10 cal/g to −50 cal/g.

3. The formulation as claimed in claim 2 wherein the endothermic cooling agent has a heat of enthalpy in the range −20 cal/g to −35 cal/g.

4. The formulation as claimed in claim 1 wherein the range of the endothermic cooling agent is 1-3%.

5. The formulation as claimed in claim 1 wherein the endothermic cooling agent is selected from the group consisting of xylitol, sorbitol, mannitol and erythritol.

6. The formulation as claimed in claim 1 wherein the one or more active agents is selected from the group consisting of hexylresorcinol, flurbiprofen, lidocaine, benzocaine, cetylpyridinium chloride, dequalinium chloride, menthol, ambroxol hydrochloride, dextromethorphan hydrobromide and guaifenesin.

7. The formulation as claimed in claim 1 wherein the formulation is selected from the group consisting of a lozenge, gel, spray, capsule, pastille, gum and tablet.

8. The formulation as claimed in claim 1 wherein said formulation contains one or more additional excipients selected from the group consisting of acidity regulators, opacifiers, colouring agents, stabilising agents, buffering agents, sweeteners, flavourings and preservatives.

9. A method of using an endothermic cooling agent having a heat of enthalpy between −10 cal/g and −100 cal/g in a composition to treat a sore throat in a person in need thereof, the method comprising administering the composition comprising the endothermic cooling agent to the person,
    wherein the endothermic cooling agent is present in the medicament at an amount in the range of 1-5% w/w.

10. A method of using an endothermic cooling agent having a heat of enthalpy between −10 cal/g and −100 cal/g for the preparation of a composition for the treatment of a sore throat in a person in need thereof, the method comprising administering the composition comprising the endothermic cooling agent to the person,
    wherein the endothermic cooling agent is present in the medicament at an amount in the range of 1-5% w/w.

* * * * *

Disclaimer

9,764,034 B2 - George Bowman, Vernon Hills; Grace Esche, Algonquin, both of Ill. BATTERY GAUGE FOR A BATTERY OPERATED INFUSION PUMP. Patent dated June 9, 1998. Disclaimer filed January 6, 2020, by the assignee, Baxter International Inc.

I hereby disclaim the following complete claims 1-4 and 9-12 of said patent.

*(Official Gazette, October 25, 2022)*